US010973775B2

(12) United States Patent
Liu et al.

(10) Patent No.: US 10,973,775 B2
(45) Date of Patent: Apr. 13, 2021

(54) ANTIBACTERIAL NANOFIBER

(71) Applicant: UNIVERSITY OF MANITOBA, Winnipeg (CA)

(72) Inventors: Song Liu, Winnipeg (CA); Sarvesh Logsetty, Winnipeg (CA)

(73) Assignee: UNIVERSITY OF MANITOBA, Winnipeg (CA)

( * ) Notice: Subject to any disclaimer, the term of this patent is extended or adjusted under 35 U.S.C. 154(b) by 0 days.

(21) Appl. No.: 16/138,577

(22) Filed: Sep. 21, 2018

(65) Prior Publication Data

US 2019/0091167 A1 Mar. 28, 2019

Related U.S. Application Data

(60) Provisional application No. 62/561,943, filed on Sep. 22, 2017.

(51) Int. Cl.
| | |
|---|---|
| *A61K 9/70* | (2006.01) |
| *D01D 5/00* | (2006.01) |
| *A61L 15/24* | (2006.01) |
| *A61P 17/02* | (2006.01) |
| *A61P 31/04* | (2006.01) |
| *A61F 13/00* | (2006.01) |
| *A61L 15/26* | (2006.01) |
| *A61K 47/32* | (2006.01) |
| *A61K 47/34* | (2017.01) |
| *A61K 9/00* | (2006.01) |
| *A61L 15/46* | (2006.01) |
| *D01F 1/10* | (2006.01) |
| *D01F 8/14* | (2006.01) |
| *D01F 8/10* | (2006.01) |
| *B82Y 30/00* | (2011.01) |

(52) U.S. Cl.
CPC ...... *A61K 9/7007* (2013.01); *A61F 13/00017* (2013.01); *A61K 9/0092* (2013.01); *A61K 9/703* (2013.01); *A61K 47/32* (2013.01); *A61K 47/34* (2013.01); *A61L 15/24* (2013.01); *A61L 15/26* (2013.01); *A61L 15/46* (2013.01); *A61P 17/02* (2018.01); *A61P 31/04* (2018.01); *D01D 5/0007* (2013.01); *D01F 1/103* (2013.01); *D01F 8/10* (2013.01); *D01F 8/14* (2013.01); *A61F 2013/00089* (2013.01); *A61L 2300/208* (2013.01); *A61L 2300/404* (2013.01); *A61L 2300/604* (2013.01); *A61L 2400/12* (2013.01); *B82Y 30/00* (2013.01)

(58) Field of Classification Search
None
See application file for complete search history.

(56) References Cited

U.S. PATENT DOCUMENTS

| | | | | | |
|---|---|---|---|---|---|
| 4,382,953 | A | * | 5/1983 | Ishii | A61K 9/0048 514/470 |
| 2002/0177139 | A1 | * | 11/2002 | Greenfield | C12N 15/1006 435/6.16 |
| 2006/0057183 | A1 | * | 3/2006 | Nakano | A61F 2/91 424/426 |
| 2010/0291182 | A1 | * | 11/2010 | Palasis | A61K 9/0024 424/426 |
| 2015/0258195 | A1 | * | 9/2015 | Almutairi | A61K 41/0028 604/20 |

OTHER PUBLICATIONS

Augustine et al., Electrospun PCL membranes incorporated with biosynthesized silver nanoparticles as antibacterial wound dressings, Appl Nanosci (2016) 6:337-344, DOI 10.1007/s13204-015-0439-1.
Bean et al., Triggered release of Bacteriophage K from agarose/hyaluronan hydrogel matrixes by Staphylococcus aureus virulence factors, Chem. Mater. 26 (2014) 7201-7208. doi:10.1021/cm503974g.
Craig et al., Bacterial protease triggered release of biocides from microspheres with an oily core, Colloids Surfaces B Biointerfaces. 127 (2015) 200-205. doi:10.1016/j.colsurfb.2015.01.036.
He et al., Fabrication of metronidazole loaded poly(e-caprolactone)/zein core/shell nanofiber membranes via coaxial electrospinning for guided tissue regeneration, J. Colloid Interface Sci. 490 (2017) 270-278. doi:10.1016/j. icis.2016.11.062.
Hoang et al., Degradation of polyethylene succinate (PES) by a new thermophilic Microbispora strain, Biodegradation. 18 (2007) 333-342. doi:10.1007/s10532-006-9067-5.
Thet et al., Prototype Development of the Intelligent Hydrogel Wound Dressing and Its Efficacy in the Detection of Model Pathogenic Wound Biofilms, ACS Appl. Mater. Interfaces. 8 (2016) 14909-14919. doi:10.1021/acsami.5b07372.
Traba & Liang, Bacteria responsive antibacterial surfaces for indwelling device infections, J. Control. Release. 198 (2015) 18-25. doi:10. 1016/j.jconrel.2014.11.025.
Xiong et al., Lipase-sensitive polymeric triple-layered nanogel for "on-demand" drug delivery, J. Am. Chem. Soc. 134 (2012a) 4355-4362. doi:10.1021/ja211279u.
Xiong et al., Bacteria-Responsive Multifunctional Nanogel for Targeted Antibiotic Delivery, Advanced Materials, 24 (46) Dec. 2012 6175-6180. doi: 10.1002/adma.201202847.

(Continued)

*Primary Examiner* — Katherine Peebles

(74) *Attorney, Agent, or Firm* — Berenato & White, LLC

(57) ABSTRACT

Bacteria-responsive core-shell nanofibers and a process for the preparation thereof are described. The nanofibers release of an antibacterial agent in response to the presence of bacteria. The core of the nanofiber comprises a biocompatible polymer together with an antibacterial agent such as a quaternary ammonium compound, for example benzyl dimethyl tetradecyl ammonium chloride (BTAC). Surrounding the core is shell comprised of a bacterially degradable polymer, which is susceptible to break-down by bacterial enzymes such as lipase, or to acidic pH conditions. The shell may comprise, for example, polycaprolactone (PCL) and poly(ethylene succinate) (PES). The nanofibers may be incorporated into wound dressings.

14 Claims, 9 Drawing Sheets

(56) References Cited

OTHER PUBLICATIONS

Yang et al., Promotion of skin regeneration in diabetic rats by electrospun core-sheath fibers loaded with basic fibroblast growth factor, Biomaterials. 32 (2011) 4243-4254. doi:10.1016/j.biomaterials.2011.02.042.

* cited by examiner

ANTIBACTERIAL NANOFIBER

CROSS REFERENCE TO RELATED APPLICATIONS

This application claims the benefit of U.S. provisional patent application No. 62/561,943 filed Sep. 22, 2017 titled "Antibacterial Nanofiber" assigned to the University of Manitoba as Applicant and named inventors Song Liu and Sarvesh Logsetty, and which is expressly incorporated herein by reference in its entirety and to which priority is claimed.

FIELD OF THE INVENTION

The present disclosure relates generally to antibacterial materials for use in wound healing.

BACKGROUND OF THE INVENTION

Wound infection is a global healthcare issue that affects the healing process. Appropriate wound dressing material can reduce the risk of infection by reducing or eliminating the invasion of pathogens. The use of antibacterial materials or agents in wound dressings can reduce risk of infection.

One approach to wound healing involves exposure of the wound to antibacterial drug release using systems that continuously elute an antibacterial agent, even if there is no bacterium present. This unnecessary release of an antibacterial agent is poorly timed with the need for the agent, and may cause undesirable cytotoxicity to the subject. Such cytotoxicity may impart delays in the healing process. Systems involving a constant and indiscriminant elution may result in a depletion of the antibacterial agent before exposure to bacteria occurs, and consequently may be ineffective when needed.

It is desirable to provide materials for use in wound healing that provide antibacterial properties when needed, in the presence of bacteria.

SUMMARY OF THE INVENTION

It is an object of the present disclosure to obviate or mitigate at least one disadvantage of previous antibacterial materials or wound healing materials.

There is provided a core-shell nanofiber comprising: a core comprising an antibacterial agent and a biocompatible polymer; and a shell surrounding the core comprising a bacterially degradable polymer.

Further, there is provided a core-shell nanofiber comprising: a core comprising benzyl dimethyl tetradecyl ammonium chloride (BTAC) and poly(vinylpyrrolidone) (PVP); and a shell comprising polycaprolactone (PCL) and poly (ethylene succinate) (PES).

A process is described for the preparation of an antibacterial core-shell nanofiber comprising: coaxially electrospinning a fiber from a core material within a shell material to thereby form the antibacterial core-shell nanofiber; wherein: the core material comprises an antibacterial agent and a biocompatible polymer; and the shell material comprises a bacterially degradable polymer.

Further A nanofiber mat and a wound dressing are described comprising the nanofiber.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
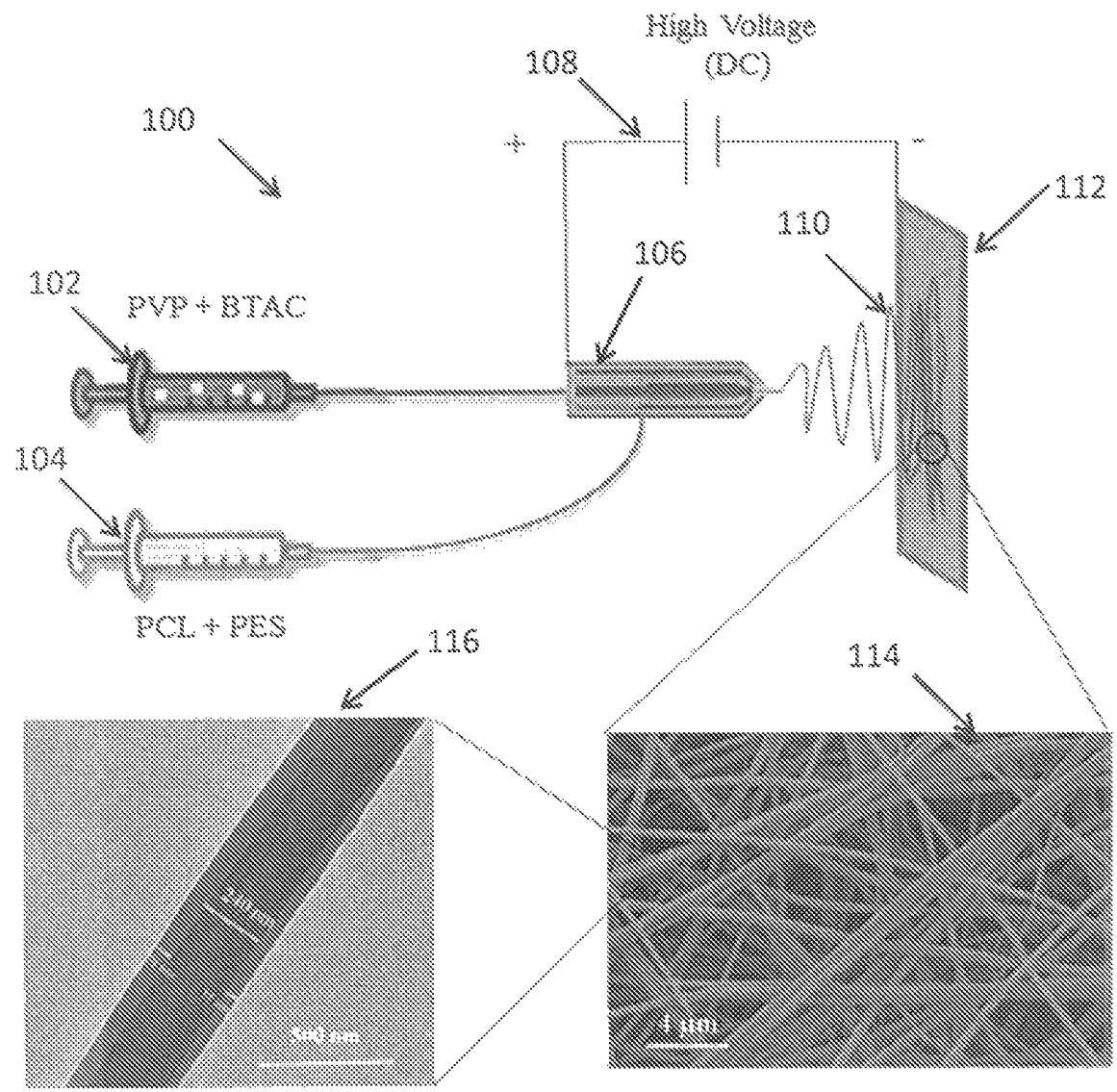
FIG. 1 is a schematic representation of the process for fabrication of nanofibers.

Generally, the present disclosure provides an antibacterial nanofiber that releases an antibacterial agent in response to the presence of bacteria.

Tackling bacterial infection without compromising wound healing can be addressed by using the antibacterial nanofibers described herein. The nanofibers may, for example, be used in preparation of bacteria responsive wound dressings.

The antibacterial nanofiber comprises a core formed of a biocompatible polymer and an antibacterial agent. The core has a very fine width, and is coated with a bacteria degradable polymer. The biocompatible polymer of the core may be a water soluble polymer.

A core-shell nanofiber is described herein. The nanofiber comprises a core comprising an antibacterial agent and a biocompatible polymer; and a shell surrounding the core comprising a bacterially degradable polymer.

The antibacterial agent may be any acceptable agent, such as a drug or biocide. For example, the agent may comprise a quaternary ammonium compound (QAC). An exemplary antibacterial agent is benzyl dimethyl tetradecyl ammonium chloride (BTAC).

The biocompatible polymer of the core may comprise any polymer that would support the antibacterial agent, and remain biocompatible, such as poly(vinylpyrrolidone) (PVP). An exemplary core may comprise BTAC and PVP.

The shell is formulated so that the bacterially degradable polymer is degraded by bacterial activity in its proximity, such as bacterial enzyme activity or by a drop in pH to 6 or less, indicative of bacterial activity. An exemplary bacterial enzyme is lipase. The polymer from which the shell is formulated is advantageously degradable by lipase. For example, the shell may comprise polycaprolactone (PCL) or poly(ethylene succinate) (PES), or both.

An exemplary core-shell nanofiber is described which comprises: a core comprising benzyl dimethyl tetradecyl ammonium chloride (BTAC) and poly(vinylpyrrolidone) (PVP); and a shell comprising polycaprolactone (PCL) and poly(ethylene succinate) (PES).

The core may consist substantially of only BTAC and PVP; and the shell may consist essentially of PCL and PES, but other components may be added to the core and the shell.

When present in the core, BTAC may be present in an amount of from about 1% to about 10%, by weight of the core, such as from 2% to 5%.

When present, the ratio of PCL to PES may be from about 1:5 to about 5:1, such as 1:1.

The ratio of the core to the shell may be from about 1:5 to about 5:1 by weight, such as from 1:2 to 2:1 by weight.

A process is provided herein for preparation of an antibacterial core-shell nanofiber. The process comprises coaxially electrospinning a fiber from a core material within a shell material to thereby form the antibacterial core-shell nanofiber; wherein: the core material comprises an antibacterial agent and a biocompatible polymer; and the shell material comprises a bacterially degradable polymer.

Optionally, the electrospinning may comprise application of a voltage from about 5 kV to about 50 kV, such as 20 kV.

Core-shell nanofibers prepared by the above process are described herein.

A nanofiber mat comprising a plurality of core-shell nanofibers is described.

An antibacterial wound dressing comprising the core-shell or the nanofiber mat may be used, as described herein.

Further, a method is described for treating a wound, the method comprising applying to the wound the antibacterial wound described herein.

A single electrospun antibacterial nanofiber is also described herein, which comprises polycaprolactone (PCL), poly(ethylene succinate) (PES), and from about 2 to 5% (by weight) TBAC as an antibacterial agent. The single electrospun fiber possesses antibacterial activity.

Single spinning may be used to fabricate bacteria responsive wound dressing for combatting bacterial infection, and for on-demand release of an antibacterial agent.

When bacteria are present in a wound, bacterial activities such as lipase secretion and release of products that act to cause an acidic pH, are able to degrade the shell polymer, exposing the core. Once the shell becomes adequately degraded, the antibacterial agent is released from the core in the location where it is needed, at a time when bacteria are present.

Wound dressings formed of or incorporating such antibacterial fibers are encompassed herein, such as may be made from other materials and impregnated or coated with the nanofibers or nanofiber mats described herein.

As referred to herein, an "antibacterial agent" encompasses a drug, a biocide, or an antimicrobial compound, which may include compounds or combinations of compounds having anti-fungal, anti-bacterial or anti-viral activity. The antibacterial agent is incorporated in the nanofiber, protected from exposure to bacteria although remaining in an active form. The agent is thus exposed, so as to assert its antibacterial properties, only on an as-needed basis.

The nanofibers described herein are bacteria responsive systems that are degraded in response to bacteria, and provide on-demand antibacterial agent release, such as drug or biocide release. More controllable release of core-shell nanofibers permits a controllable release, while single nanofibers provide efficient and prolonged bacteria killing activity. The selective release of antibacterial agents by these nanofibers and efficacy against bacteria was accompanied by high viability of mammalian cells tested. Thus, efficient antibacterial activity of nanofibers without comprising wound healing makes these nanofibers advantageous for use in wound dressings to avoid or alleviate wound infections, and in other applications where antibacterial activity is required.

Example 1

Bacteria-Responsive Nanofibers for On-Demand Release of Antibacterial Agents to Address Wound Infections Abstract.

Nanofibers have been used as biocompatible materials for wound healing in recent years. In this example, core-shell nanofibers are prepared and used to provide triggered release of an antibacterial agent. Due to bacterial activity, such as lipase secretion and acidification of pH, degradation of the shell material was facilitated and resulted in the release of an incorporated antibacterial agent present in the core of the nanofiber. Bacteria triggered release of an antibacterial agent can advantageously replace other antibacterial strategies that deploy unneeded release of antibacterial agents and which may result in cytotoxicity to a subject. The nanoscopic and core-shell structure of the nanofibers were finely confirmed by scanning electron microscopy (SEM) and transmission electron microscopy (TEM). Due to bacterial activity, nanofibers were degraded in bacterial supernatant at significantly higher levels than in non-enzymatic solutions. Moreover, bacteria responsive core-shell nanofibers showed a more controllable release of the antibacterial agent, which resulted in prolonged effective antibacterial efficacy, and lower cytotoxicity to fibroblast cells.

Introduction.

Skin injuries especially chronic wounds are a global healthcare issue and the healing process of a wound is highly influenced by the wound dressing material. The use of antibacterial agents to eliminate invasion and colonization of pathogens in a wound is an important aspect in the wound dressing. Antibacterial agents have been incorporated into different biomaterials for antibacterial activity (Augustine et al, 2016). Previous approaches to the design of antibacterial releasing systems have involved continuous release of bioactive compounds, even if no bacteria is present. This unneeded release of antibacterial agents could cause undesirable cytotoxicity, which can delay the healing process. Further, continuous elution may deplete the system of its antibacterial agent before infection occurs. This would render such systems ineffective, and poses additional pressure on healthcare costs. Treatment failure and prolonged therapy may be the result of such systems (Craig et al., 2016). Therefore, it is important to address infection without compromising wound healing.

To reduce the misuse and overuse of antibacterial agents, a bacteria-responsive system may be used. Bacteria possess different virulence factors, which can act as triggers for such systems (see, for example Thet et al., 2016; and Traba & Liang 2015). As a result, a system would release its antimicrobial payload only when interacting with bacteria. Enzymes are a virulence factor that may be used to trigger a bacteria responsive systems. For example, hyaluronidase enzymes secreted by *S. aureus* have been used for triggering release of bacteriophage K embedded in a photo-cross-linkable hyaluronic acid based hydrogel (Bean et al., 2014).

In *S. aureus*, the protease enzyme was used to stimulate degradation of polypeptide based drug-loaded particles (Craig et al., 2015).

Unlike hyaluronidase enzyme which is mostly secreted by Gram-positive bacteria with little to no excretion in gram negative bacteria, lipase is secreted by both Gram-positive and Gram-negative bacteria. As compared to protease enzyme that naturally presents in extracellular matrix (ECM) and is secreted by white blood cells in the wound site, lipase is mostly the product of bacteria.

Lipase-labile bonds, such as fatty acid esters or anhydrides can be degraded in response to lipase. Polycaprolactone (PCL) is a biodegradable polyester with the low hydrolytic degradation. A lipase sensitive triple-layered nanogel (TLN) has been used as a carrier for on-demand drug delivery (Xiong et al., 2012a). In this approach, the TLN contained a PCL interlayer between the cross-linked polyphosphoester core and the shell of poly(ethylene glycol). The PCL fence of TLN was subjected to degradation by the activity of bacterial lipases.

A rapid rate of response is desirable. The faster a system responds to a triggering factor secreted by bacteria, the more effective the system will be. The rate of response is dependent on both physical and chemical structure of the system. Systems with a large surface area such as nanoparticles and nanofibers, may be triggered faster.

In the system described in this example is an electrospun polymeric nanofiber having high porosity and excellent pore interconnectivity. This system leads to advantages for use in wound dressing materials. The nanofiber described permits intimate contact with wound areas despite highly variable or irregular wound shapes and sizes. Thus, the protection of an open wound from external physical pressures and contamination would be facilitated using the described nanofiber. Further, a greater opportunity for the self-healing process to occur, and lower risk of scar formation is provided by the described nanofiber. Permeability of the nanofiber, and of wound dressings made from the nanofiber, to moisture and air allows the extraction of wound exudate to provide a moisturized environment and prevent infection.

Polycaprolactone (PCL) has the advantage of being a biodegradable synthetic polymer, with excellent biocompatibility and efficacy both in vitro and in vivo. However, its highly hydrophobic nature and slow degradation has previously hindered its use in biomedical applications, such as in wound dressings. To overcome this limitation, PCL can be blended with another biodegradable polymer. Poly(ethylene succinate) (PES) is an aliphatic biodegradable polyester, which has higher rate of degradation than PCL (Hoang et al., 2007).

In this example, electrospun nanofibrous mats are prepared based on PCL and PES, with effective degradation in response to bacteria.

Single electrospun nanofibers are prepared, which due to the superficial effect in a nanoscale size, the antibacterial agent (drug) particles in the single electrospun nanofibers tend to accumulate on the surface of the fibers prepared. Therefore, a large amount of the antibacterial agent is released at the initial stage of bacterial infection in an uncontrolled manner. As a consequence, whenever an infection lasts for a prolonged time, much of the antimicrobial content of wound dressing may have been released in early stage of infection. These main drawbacks in the use of antimicrobial wound dressings can be avoided through the use of core-shell nanofibers fabricated through co-axial electrospinning (He et al., 2017; Yang et al., 2011).

In this example, two immiscible solutions are pushed through two concentrically located needles that form a single outlet. As the solutions are pumped out of the needles, the outer polymer (or "shell") material covers the inner (or "core") material, which comprises an antimicrobial agent or drug. As a result, the polymer nanofibers so formed have a core-shell structure. Drug preservation in the core material prevents the uncontrolled release of the drug, and ensures even distribution of the drug, which leads to prolonged antimicrobial efficacy.

The core-shell nanofibers prepared have a PCL/PES shell, and contain as a drug within the core: benzyl dimethyl tetradecyl ammonium chloride (BTAC) for antibacterial activity. In the core material, the BTAC is dissolved in poly(vinylpyrrolidone) (PVP), which serves as core. The nanofibers form nanofiber mats, which have the potential to be degraded in response to bacteria. Drug release and antibacterial efficacy of single and core-shell nanofibers are compared. Morphology, diameter, and the core-sell structure of nanofibers are evaluated using SEM and TEM. Cytotoxicity of the nanofibers was evaluated.

Materials and Methods.

The described nanofiber comprises a shell of polycaprolactone and poly(ethylene succinate); and a core of poly (vinylpyrrolidone) as the core polymer and benzyl dimethyl tetradecyl ammonium chloride (BTAC) as the core antibacterial agent. Bacterial activity, comprising lipase secretion and acidic pH, was used to degrade the shell. Once the shell became adequately degraded, the antibacterial agent was released from the core. Further details are outlined below.

Materials

Polycaprolactone (PCL) 80,000 MW, poly(ethylene succinate) (PES) 10,000 MW, poly(vinylpyrrolidone) (PVP) 40,000 MW, dimethylformamide (DMF), dichloromethane (DCM), benzyl dimethyl tetradecyl ammonium chloride (BTAC) as an antibacterial drug, 3-(4,5-Dimethyl-2-thiazolyl)-2,5-diphenyl-2H-tetrazolium bromide (MTT), dimethyl sulfoxide (DMSO), and orange II sodium salt were purchased from Sigma.

The structure of the polymers is as shown below.

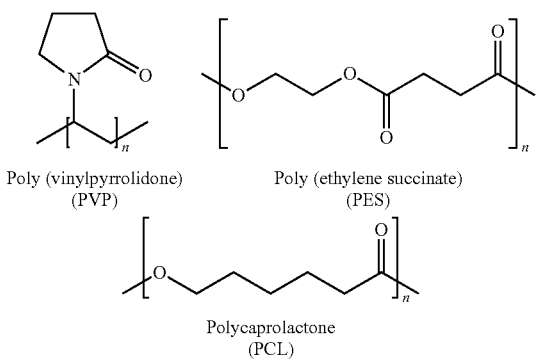

Poly (vinylpyrrolidone) (PVP)   Poly (ethylene succinate) (PES)

Polycaprolactone (PCL)

An Inoveso electrospining apparatus (Model Ne300, Turkey), was used to fabricate single and core-shell nanofibers. *Staphylococcus aureus* (*S. aureus*-ATCC 29213) and *Escherichia coli* (*E-coli*—ATCC 25922) were used as gram positive and gram negative bacteria. ATCC-PCS-201 neonatal human dermal fibroblast was purchased from Cedarlane Corporation, Canada.

Fabrication of Nanofibers

PCL and PES were dissolved in DCM:DMF (4:1) at a concentration of 8 wt % uncontrolled manner and 20 wt %.

PCL solution (8 wt %) was mixed with PES solution (20 wt %) in volume ratios of (PCL:PES) 5:1, 2:1, and 1:1. Then, the mixed solutions were subjected to the single electrospinning experiment. Voltage (20 kV), flow rate of solution (1 mL/h), and distance between syringe and collector (18 cm) were set for each of the samples.

For core-shell electrospinning, PVP was considered as core component and the same solution in the single nanofibers as shell component. PVP was dissolved in DCM:DMF (4:1) at a concentration of 15 wt %. Flow rates of core and shell solution were 0.3 and 1 ml/h, respectively.

To prepare drug loaded nanofibers, BTAC was dissolved in DCM and added to PCL/PES blend for single nanofibers or to PVP for core-shell nanofibers. 2.5%, 3.5%, and 4.5% of BTAC with respect to weight of whole polymer was used to study the antibacterial efficacy of nanofibers. The sample codes are listed in Table 1.

TABLE 1

Feed composition of fabricated nanofibers

| Sample code | Feed composition |
|---|---|
| PCL:PES 5:1 | PCL 8% + PES 20% |
| PCL:PES 2:1 | |
| PCL:PES 1:1 | |
| S 2.5 | Single electrospining: |
| S 3.5 | PCL 8% + PES 30% (1:1) + 2.5, 3.5, and 4.5% BTAC |
| S 4.5 | |
| CS 2.5 | Co-axial electrospining: |
| CS 3.5 | Shell: PCL 8% + PES 30% (1:1) |
| CS 4.5 | Core: PVP 15% + 2.5, 3.5, and 4.5% BTAC |

FIG. 1 shows a schematic representation of the process (100) for fabrication of nanofibers. Briefly, a blend of PVP and BTAC is provided in a core syringe (102), while a blend of PCL and PES is provided in the shell syringe (104), which are combined in a common extruding syringe (106), subjected to a voltage (108) of 20 kV, and the nanofiber (110) was collected at a collector (112). A photomicrograph of the nanofiber mat (114) formed and of an individual fiber (116) are shown.

Figure 2:
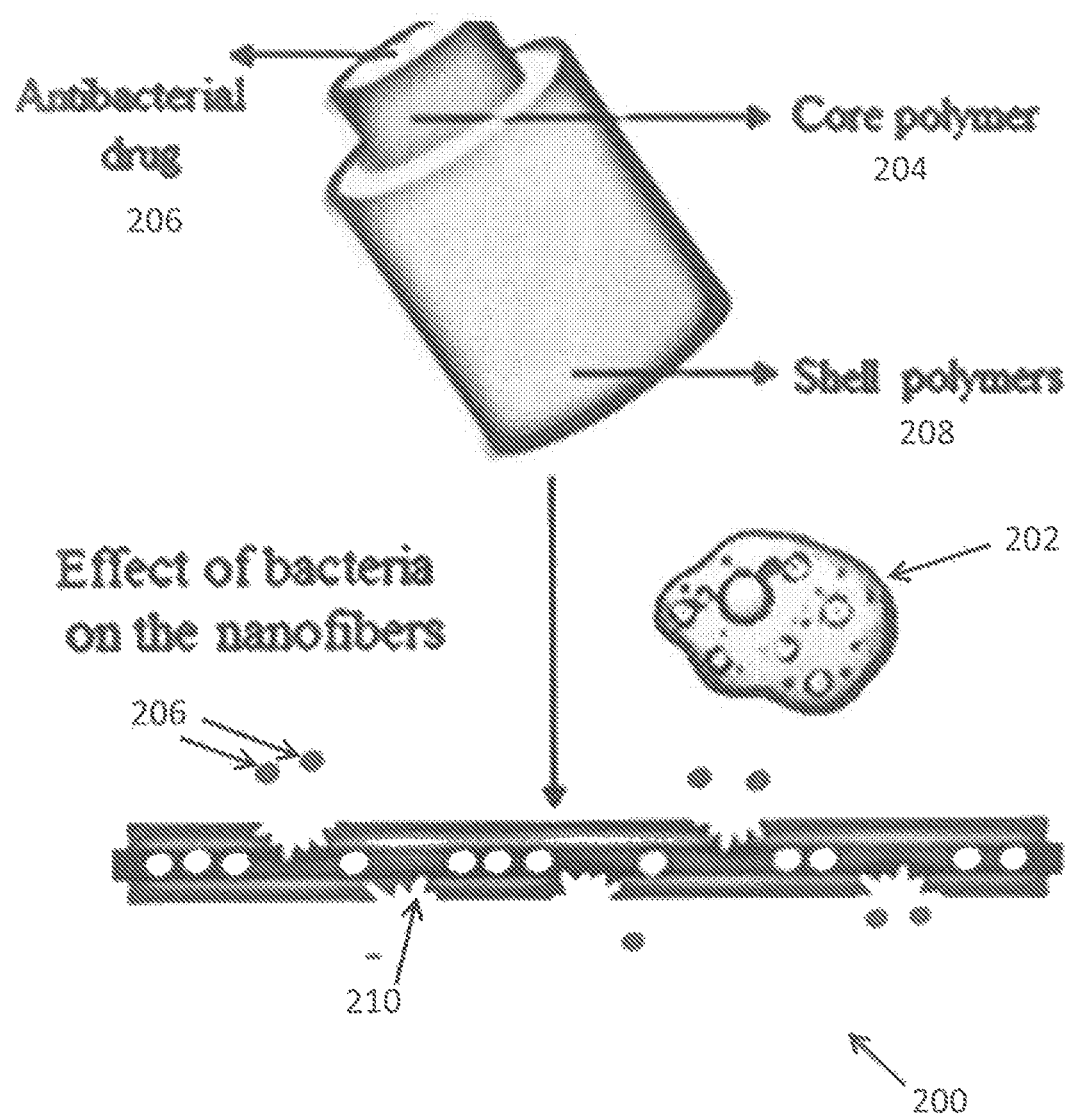
FIG. 2 is an illustration of a core-shell nanofiber, and an overview of the degradation process by bacteria.

FIG. 2 provides a diagrammatic illustration of the resulting nanofiber, and an overview of the degradation process (200) by bacteria (202). The nanofiber comprises the core polymer (204) which contains an antibacterial drug (206), and the shell polymer (208). Upon exposure to the bacteria (202) a degraded fiber (210) is formed, from which the antibacterial drug (206) is slowly released.

Morphology of Nanofibers

Morphology and diameter of nanofibers were studied by secondary electron microscope (SEM, FEI Nova NanoSEM 450). To visualize the effect of bacterial activity on degradation of nanofibers, fibers were immersed in bacterial supernatant solution and Tryptone Soya broth (TSB) for 72 h, and observed them under SEM. 18 h cultured bacteria ($10^8$ CFU mL$^{-1}$) were used to prepare the supernatant. The supernatant was centrifuged from 18 h culture (5000 rpm for 15 min) and then filter-sterilized (0.22 μm filters) before storage at 4° C.

The core-shell structure of the prepared nanofibers was characterized by transmission electron microscopy (JEOL JEM-2100F) at an accelerating voltage of 200 kV, for which carbon-coated copper grids were used to collect the nanofibers.

Drug Release Measurement

To study the drug release, nanofibers were immersed in bacterial supernatant and TSB (4 mg in 2 mL media) and incubated at 37° C. To obtain the cumulative release of BTAC, 600 μL of eluted drug medium was removed for quantification; this volume replaced with fresh supernatant to provide sink conditions. Removed media was mixed with 0.25 mL orange II dye solution. After 5 min, 600 μL chloroform was added to the dye-BTAC complex, and the mixture was vortexed for 45 s to ensure that the chloroform and dye were mixed thoroughly. 600 μL of the chloroform phase (the bottom layer) was removed into a UV silica cuvette, and the absorbance was measured at 485 nm. The structures of (a) orange II dye and (b) BTAC are shown below.

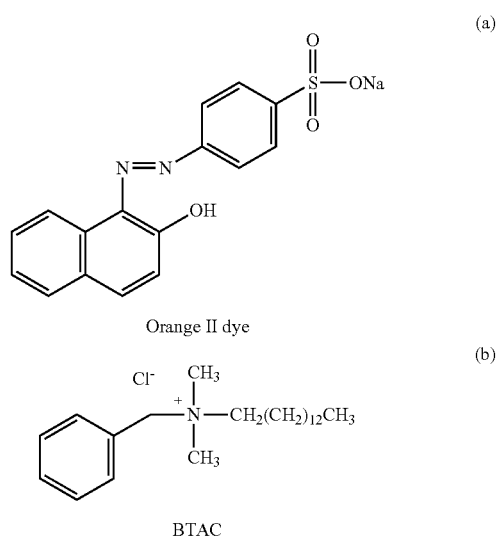

Antibacterial Test

The antibacterial activity of the nanofiber mats was tested by colony counting method against *Staphylococcus aureus* (*S. aureus*) and *E. coli*, which are commonly found on burn wounds. For the antibacterial studies, logarithmic-phase cultures were prepared by initially suspending several colonies in phosphate buffered saline (PBS, 0.1 M, pH 7.4) at a density equivalent to a 0.5 McFarland standard of $1 \times 10^8$ colony forming units (CFU) mL$^{-1}$ and then diluted 100 times to $1 \times 10^6$ CFU mL$^{-1}$. 15 μL of the diluted *E-coli* and *S. aureus* suspension was further diluted into 45 mL cation-supplemented MuellerHinton (MH) broth and TSB, respectively. After culturing in the incubator at 37° C. for overnight, the concentration of bacteria went up to $10^8$ CFU mL$^{-1}$.

2 mL of bacteria suspension was added to 4 mg of nanofibers and incubated. At the predetermined contact times, 150 μL of bacteria culture was taken from the flask, neutralized, and decimal serial dilutions with PBS were repeated with each initial sample. 30 μL of the diluted sample was then spread onto four zones of a Tryptone Soya agar plate (CM 0131, OXOID). After incubation of the plates at 37° C. for 18 h, the number of viable bacteria (colonies) was counted manually for control (A, bacteria suspension without sample) and BTAC-loaded nanofibers (B). Bacteria reduction was reported as percentage and Log 10. The percentage reduction of bacteria (%)=(A−B)/A× 100; and logarithm reduction=log (A/B).

Cytotoxicity Tests

An in vitro cytotoxicity assay was conducted on fibroblast cells (ATCC-PCS-201 neonatal human dermal fibroblast) to evaluate the effect of drug-loaded nanofibers. Nanofibers were cut in to the same shape and weighted to 4 mg (triplicate). They were pre-soaked in 1 mL of ethanol for 10 min. Samples were exposed to UV light for 45 min (each side). Fibroblast cells were cultured in 24 well-plates at density of $1 \times 10^5$ (cell/mL). After reaching to 90% confluence, 2 mL of fibroblast culture medium was added to each of the wells and the dressings. Afterwards, the cells were incubated at 37° C. for 24 h. Cell viability was determined using MTT assay after removal of dressings. Each well received 500 μL of 1:10 (v/v) MTT and fibroblast medium solution. Subsequently, after 2 h incubation at 37° C., the culture medium with the MTT solution were aspirated and replaced by 500 μL DMSO. Finally, 100 μL aliquots from each well (in triplicate) were transferred to 96-well plates and viability of cells was evaluated using spectrophotometer at 570 nm wavelength (PowerWave™ XS2 Microplate Spectrophotometer, BioTek Instruments Inc., Canada).

Results and Discussion.

In summary, the BTAC-loaded core-shell nanofibers significantly inhibited *Staphylococcus aureus* and *Escherichia coli* growth over 2 hours. The core-shell structure provided the more controlled release of BTAC and prolonged antibacterial properties, as compared to single nanofibers. The core-shell nanofibers exhibited minimal cytotoxicity against fibroblast cells, with greater than 80% viable cells remaining after 24 hours of contact. The tested core-shell nanofibers can be used for on-demand release of antibacterial agents effective against lipase-secreting bacteria.

The exceptional properties of these bacteria responsive core-shell nanofibers, which degraded in response to the presence of bacteria, can provide on-demand biocide release. Core-shell nanofibers are capable of a controllable release, and can provide efficient and prolonged bacterial killing activity as needed, when bacteria are present. However, the delay in the initiation of release until such bacteria are present provides an advantage that no antibacterial agent is deployed when it is not needed. The selective release of antibacterial agent from the core-shell nanofibers permitted the exposed fibroblast cells to maintain high cell viability. Efficient antibacterial activity of nanofibers, without comprising wound healing, makes core-shell nanofibers advantageous systems to approach a reduction in wound infections.

Morphology of Electrospun Nanofibers

SEM photos were taken to study the morphology of nanofibers.

Figure 3:
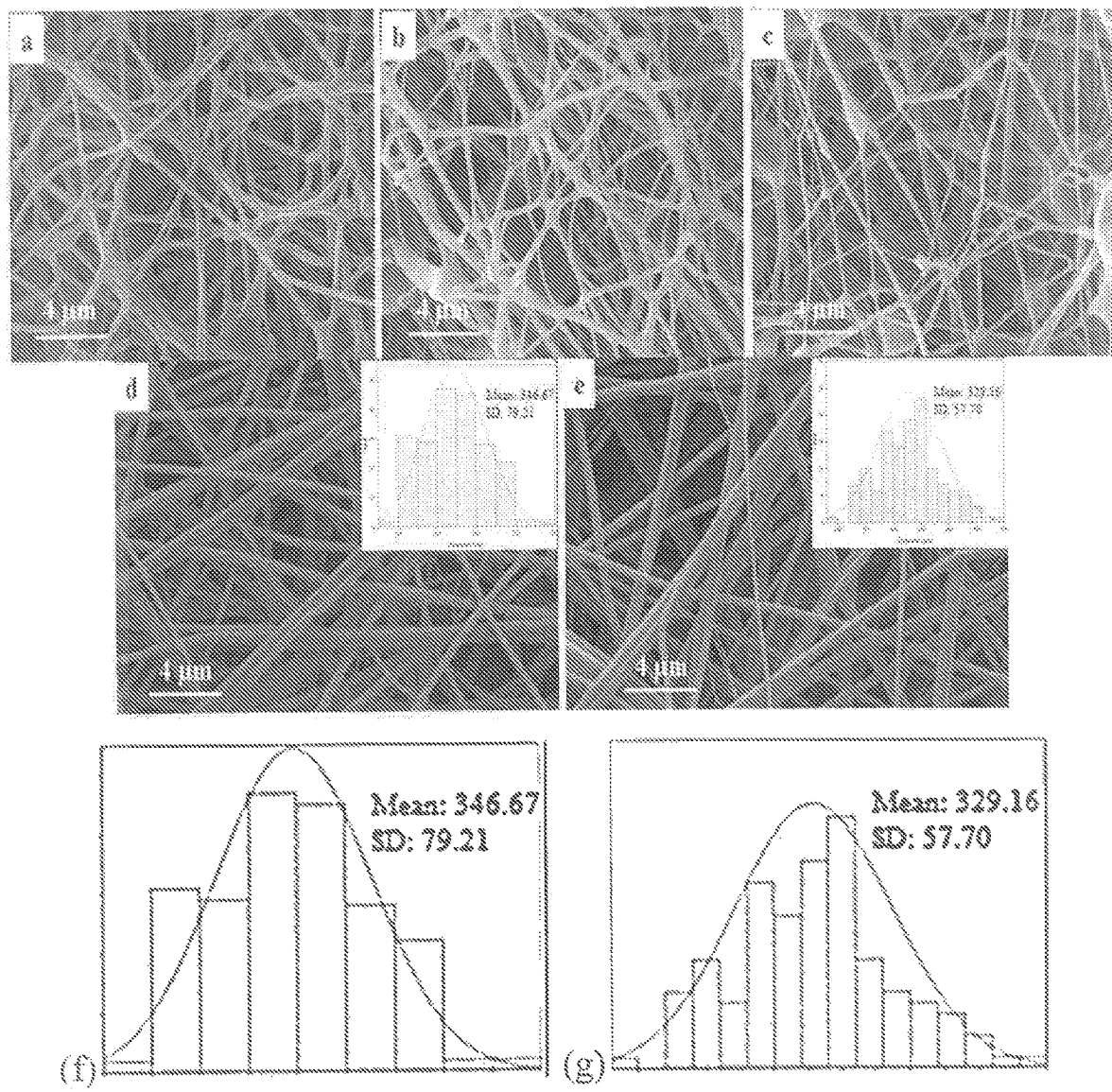
FIG. 3 shows the morphology of nanofibers with different ratios of PCL:PES in Panels (a) to (c); different CS/PCL-PES or S/PCL-PES values in Panels (d) and (e); and distribution curve of fiber diameter in Panels (f) and (g).

FIG. 3 shows the morphology of nanofibers with different ratios of PCL. Panel (a) shows PCL:PES 5:1; Panel (b) shows PCL:PES 2:1; Panel (c) shows PCL-PES 1:1; Panel (d) shows CS/PCL-PES (30%)/1:1/2.5% BTAC; Panel (e) shows S/PCL-PES (30%)/1:1/2.5% BTAC. Panel (f) shows a larger version of the inset distribution curve of panel (d) showing a mean diameter of 346 nm (+79.21 SD); and Panel (g) shows a larger version of the inset distribution curve of panel (e) showing a mean diameter of 329.16 nm (+57.70 SD).

The PES solution that was used in the nanofibers had 20% primary concentration. All the ratios reflected the merged morphology. FIG. 3, Panel (c) that related to PCL-PES 1:1, had a higher ratio of PES than other samples. Due to relatively lower molecular weight of PES than PCL, the higher the amount of PES in the polymer solution resulted in lower spinability and more beads.

Increasing the concentration of PES from 20% to 30% caused a significant changed in the morphology of the nanofibers. As can be seen in the FIG. 1, Panel (d) and Panel (e), the morphology of core-shell and single nanofibers changed from bead-and-string to a completely fibrous structure. A 1:1 ratio for PCL:PES is preferable to other ratios, because of higher degradability of PES than PCL. Thus, this concentration and ratio were maintained in all of the following experiments.

Both single and core-shell drug-loaded nanofibers showed a nano-sized diameter. As it was expected, core-shell nanofibers had a slightly higher diameter (346 nm) than single ones (329 nm), because of higher syringe internal diameter (inner diameter for shell in core-shell syringe: 1.2 mm; and for single syringe: 0.8 mm).

To confirm the core-shell structure of nanofibers, TEM photos of drug loaded nanofibers (shell: PCL/PES, core: PVP/2.5% BTAC) were taken. To prepare the sample, polymer solution was directly electrospun on carbon coated cupper grids. The micrographs clearly showed the core-shell structure of nanofibers. A sharp boundary between shell and core along the length of the fiber was present, which was due to different viscosity of core and shell solution and partial-immiscibility. The presence of nitrogen in PVP and BTAC could enhance the TEM contrast over that of PCL/PES.

Figure 4:
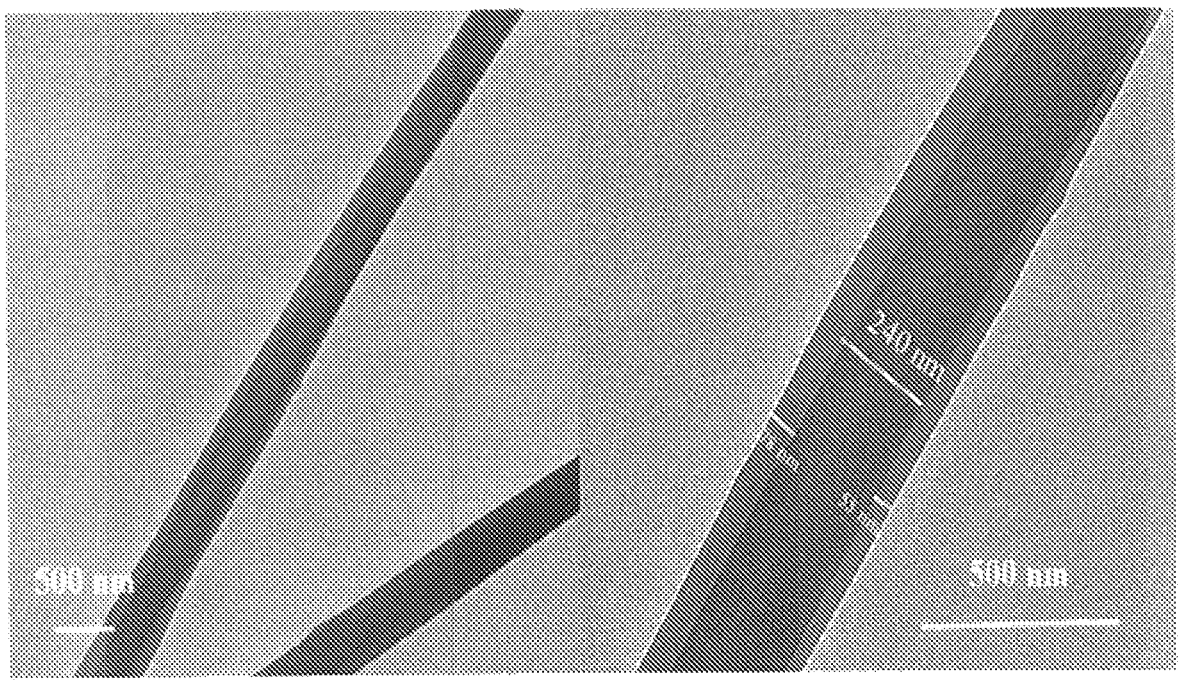
FIG. 4 shows two exemplary TEM photos of the drug loaded antibacterial nanofiber.

FIG. 4 shows two exemplary TEM photos of the drug loaded antibacterial nanofiber (shell: PCL/PES, core: PVP, 2.5% BTAC), with the right side photo being more highly magnified than the left side photo.

To better understand the effect of PES on the degradation, nanofibers were immersed in TSB and bacterial supernatant for 72 h and were studied using SEM photos. Different degradability of PCL and PES could be observed.

Figure 5:
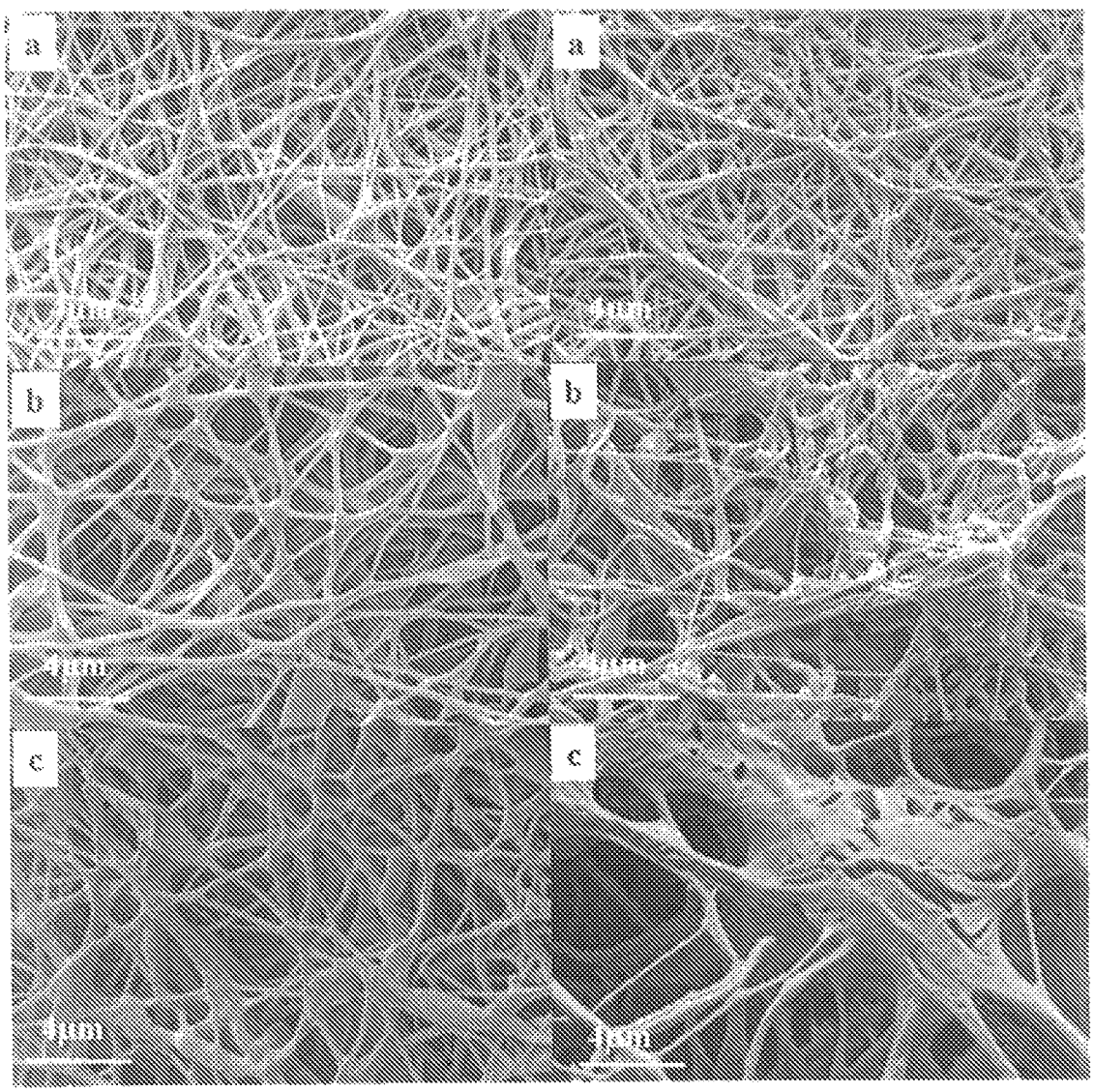
FIG. 5 illustrates the morphology of nanofibers immersed in TSB (left-side) and supernatant (right-side) during 72 h; Panel (a) shows PCL, Panel (b) shows S/PCL:PES, and Panel (c) shows CS/PCL: PES.

FIG. 5 illustrates the morphology of nanofibers immersed in TSB (left-side) and supernatant (right-side) during 72 h; Panel (a) shows PCL, Panel (b) shows S/PCL:PES, and Panel (c) shows CS/PCL: PES.

Different degradability of PCL and PES is emphasized by comparison of Panels (a) and (b). Nanofibers containing PES showed higher disintegration than PCL after immersion in media. That was the reason that we chose the nanofibers with higher ratio of PES (1:1). On the other hand, bacterial supernatant had significant impact on degradation of nanofibers containing PES. Bacterial activity caused enzymatic degradation of ester linkage in the PES nanofibers. This observation was consistent with the study by Hoang et al., (2007) which compared enzymatic biodegradation of PES, PCL, and poly (3-hydroxybutyrate) (PHB) in the form of films. PES films showed rough surfaces and small cracks in the inoculated culture after 2 days. PHB and PCL films were degraded within 6 days, however the rate of their degradation was lower than PES.

Drug Release Measurements

Nanofibers were immersed in bacteria supernatant and TSB and their drug release was measured using spectrophotometry method during 24 h.

Figure 6:
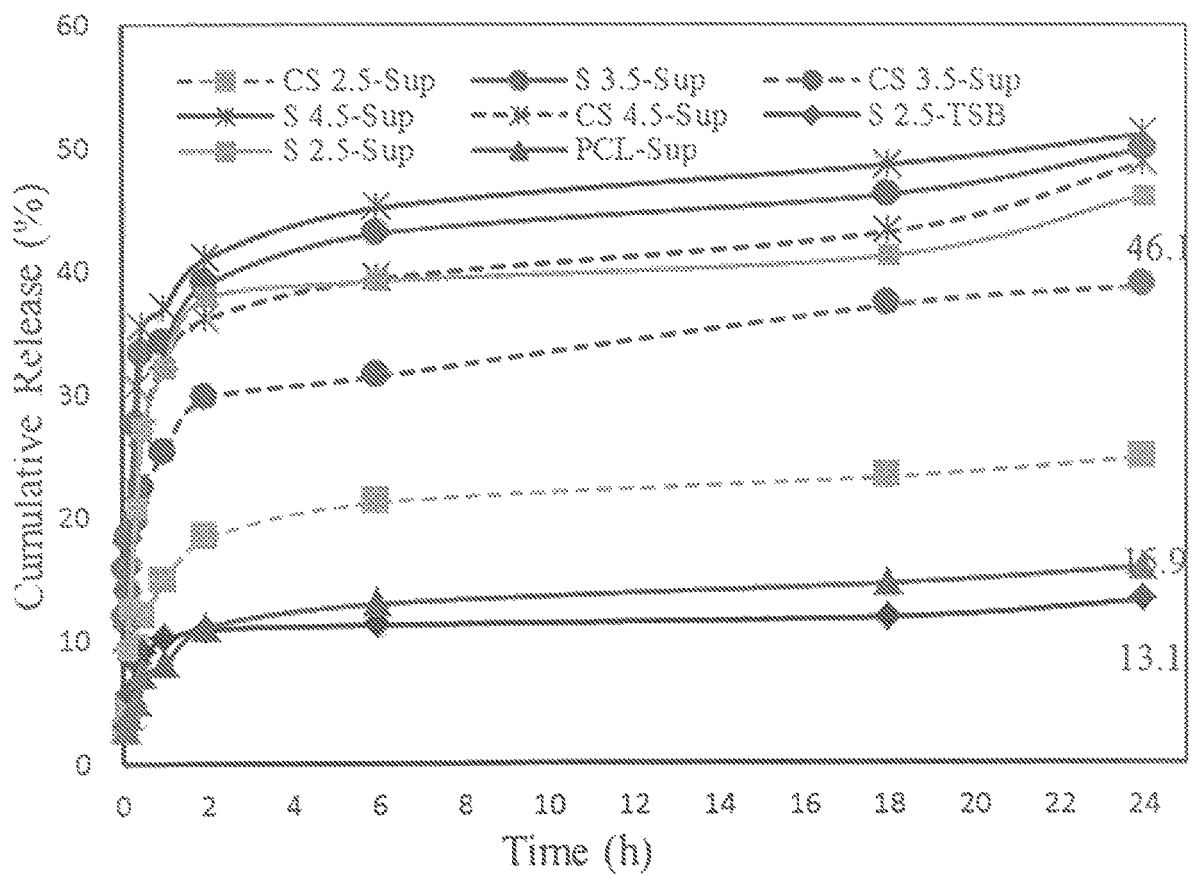
FIG. 6 shows the cumulative release of single and core-shell nanofibers.

FIG. 6 shows the cumulative release of single and core-shell nanofibers (solid lines: single nanofibers, dash lines: core-shell nano-fibers), illustrating that the release of BTAC in TSB (13.1% for S 2.5) is much lower than release in bacteria supernatant (46.1% for S 2.5), which was due to bacterial activity (P-value: 0.0001). Besides, comparison of cumulative release between PCL 2.5 (15.9%) and S 2.5 (46.1%) in supernatant significantly showed the role of PES in the degradation. S 2.5 was fabricated through blending the PCL and PES with 1:1 blend ratio. These results were consistent with degradation study by SEM. Higher degradation rate of PES than PCL, significantly affected the cumulative release of BTAC. It is worthy of mention that all the core-shell nanofibers displayed less cumulative release percentage than single equivalents, which mostly related to lower burst release in the first 2 h.

The slow release was due to the fact in the core-shell nanofiber release was dependent on (1) degradation of the shell in presence of enzyme and (2) dissolution of PVP as the matrix polymer in the core. In addition, more controllable release in core-shell nanofibers compared to single nanofibers was obvious in the first 2 h. Less burst release for CS 2.5 could be observed compared with S 2.5 (the slope of graph is lower in the first 2 h). This controllable release could cause later depletion of BTAC. This observation indicated effective encapsulation of BTAC into the core. Core-shell nanofibers could keep the antibacterial properties for longer time. This feature also could decrease the cost associated with wound healing. The core-shell structure alleviates the initial burst release and prolongs the release period. However, for single nanofibers formed using a traditional blending electrospinning system, the drug was simply incorporated into ultrafine fibers by dispersing particles into the polymer solution directly. Thus, the agents might migrate fast to the surface or near the surface of the fibers during the electrospinning process, which would lead to severe initial burst release of the loaded drugs. The severe burst release then could lead to excessive initial drug delivery and affect long term antibacterial properties.

Antibacterial Activity

The design of an antimicrobial and biocompatible wound dressing was evaluated. BTAC was chosen from among many possible antibacterial compounds for use in the present Example. Use of other antibacterial compounds is anticipated. Quaternary ammonium (QA) salts are well-known as efficacious biocides against microorganisms including bacteria, and fungi. Given their amphiphilic nature, QACs demonstrate a detergent-like mechanism of action against microbial life. Electrostatic interactions between the positively charged QAC head and the negatively charged bacterial cellular membrane are followed by permeation of the QAC side chains into the intramembrane region, ultimately leading to leakage of cytoplasmic material and cellular lysis.

Table 2 and Table 3 show the antibacterial efficacy of the nanofiber with different formulations against *S. aureus* and *E. coli* with ~8 Log CFU/mL concentration.

TABLE 2

Antibacterial activity of *S. aureus* against nanofibers with different formulations and different contact times.

| | | Contact time (min) | | | | | |
|---|---|---|---|---|---|---|---|
| | | 5 | 10 | 20 | 30 | 60 | 120 |
| CS 2.5 | % | 45.7 ± 3.7 | 61.6 ± 4.7 | — | 82.8 ± 3.9 | 96.1 ± 1.0 | 97.9 ± 0.3 |
| | $Log_{10}$ | | | | | 1.4 ± 0.2 | 6.6 ± 0.3 |
| S 2.5 | % | 67.3 ± 8.5 | 88.7 ± 1.7 | — | 94.6 ± 3.0 | 97.6 ± 0.8 | 100.0 |
| | $Log_{10}$ | | | | | 1.6 ± 0.3 | 8.8 |
| CS 3.5 | % | 78.4 ± 6.9 | 88.3 ± 1.5 | — | 99.5 ± 0.5 | 99.9 ± 0.1 | 100.0 |
| | $Log_{10}$ | | | | 2.1 ± 0.2 | 2.9 ± 0.4 | 8.8 |
| S 3.5 | % | 75.3 ± 1.3 | 90.7 ± 0.8 | 99.5 ± 0.8 | 99.7 ± 0.4 | 100.0 | 100.0 |
| | $Log_{10}$ | | | 2.3 ± 0.4 | 2.6 ± 0.3 | 8.8 | 8.8 |
| CS 4.5 | % | 99.6 ± 0.3 | 100.0 | — | | | |
| | $Log_{10}$ | 2.4 ± 0.2 | 8.9 | | | | |
| S 4.5 | % | 100.0 | — | | | | |
| | $Log_{10}$ | 8.9 | | | | | |
| PCL 2.5 | % | 34.4 ± 6.6 | 47.7 ± 6.8 | 50.4 ± 4.0 | 58.0 ± 2.9 | 65.5 ± 6.6 | 83.9 ± 1.3 |
| | $Log_{10}$ | | | | | | |
| BTAC | % | 96.1 ± 0.2 | 98.5 ± 0.9 | 100.0 | — | | |
| | $Log_{10}$ | 1.4 ± 0.2 | 1.8 ± 0.3 | 8.9 | | | |

TABLE 3

Antibacterial activity of *E. coli* against nanofibers with different formulations and different contact times.

| | | Contact time (min) | | | | | |
|---|---|---|---|---|---|---|---|
| | | 5 | 10 | 20 | 30 | 60 | 120 |
| CS 2.5 | % | 7.9 ± 0.9 | 15.5 ± 3.1 | — | 53.0 ± 5.2 | 60.3 ± 5.2 | 96.9 ± 0.5 |
| | $Log_{10}$ | | | | | | 1.5 ± 0.1 |
| S 2.5 | % | 14.9 ± 3.8 | 26.3 ± 3.1 | — | 74.0 ± 2.0 | 78.6 ± 3.6 | 98.9 ± 0.4 |
| | $Log_{10}$ | | | | | | 2 ± 0.1 |
| CS 3.5 | % | 27.2 ± 1.4 | 37.1 ± 1.82 | — | 94.8 ± 0.5 | 95.2 ± 0.4 | 100 |
| | $Log_{10}$ | | | | | 1.3 ± 0.1 | 8.9 |
| S 3.5 | % | 38.9 ± 3.8 | 49.1 ± 3.1 | 61.6 ± 4.2 | 96.3 ± 0.6 | 97.1 ± 0.4 | 100 |
| | $Log_{10}$ | | | | 1.4 ± 0.2 | 1.5 ± 0.1 | 8.9 |
| CS 4.5 | % | 45.9 ± 0.9 | 60.8 ± 3.5 | 70.2 ± 1.7 | 97.0 ± 0.3 | 99.3 ± 0.2 | 100 |
| | $Log_{10}$ | | | | 1.5 ± 0.1 | 2.2 ± 0.3 | 8.9 |
| S 4.5 | % | 57.3 ± 4.3 | 64.9 ± 2.3 | 76.6 ± 3.0 | 97.8 ± 0.1 | 100.0 | 100 |
| | $Log_{10}$ | | | | 1.7 ± 0.0 | 8.9 | 8.9 |
| PCL 2.5 | % | 5.7 ± 2.9 | 12.0 ± 1.8 | 24.0 ± 4.6 | 38.3 ± 6.8 | 48.7 ± 5.6 | 47.8 ± 3.2 |
| | $Log_{10}$ | | | | | | |
| BTAC | % | 95.3 ± 0.3 | 96.0 ± 0.2 | 98.8 ± 0.5 | 100.0 | | |
| | $Log_{10}$ | 1.3 ± 0.0 | 1.4 ± 0.1 | 1.9 ± 0.1 | 8.9 | | |

According to the results achieved, antibacterial activity of the nanofibers progressively increased as the contact time increased. As experimentally demonstrated, all the core-shell nanofibers showed less bacteria inhibition than single nanofibers. The hydrophobic nature of the shell (PCL and PES) could effectively retard the penetration of water into the fibers and thereby prolong the release period of BTAC and consequently the antibacterial efficacy over time. It is worth noting that antibacterial activity of nanofibers against S. aureus as Gram-positive bacteria is higher than Gram-negative bacteria (E. coli), which is due to outer membrane containing lipopolysaccharides in gram-negative bacteria. Because QACs target the bacterial cell membrane, they can be considered to be broad-spectrum antibiotics though they exhibit markedly increased activity against Gram-positive bacteria. Gram-positive bacteria possess a single phospholipid cellular membrane and a thicker cell wall composed of peptidoglycan, Gram-negative bacteria are encapsulated by two cellular membranes and a rather thin layer of peptidoglycan. It is due to the presence of this second membrane that QACs and other membrane-targeting antiseptics tend to exhibit decreased activity against Gram-negative species.

The antibacterial property of free BTAC was evaluated and compared with the result for BTAC-loaded nanofibers. The concentration of free BTAC was equivalent to cumulative release of S 3.5 within 2 h. S 3.5 obtained 100% bacteria inhibition against S. aureus and E. coli, within 30 and 120 min, respectively. However, faster bacteria killing activity was observed for free BTAC against both bacteria. Free BTAC obtained 100% bacteria inhibition before 60 min. Thus, prolonged and efficient antibacterial properties cannot be expected if free drug is used. This fact is important, when the cytotoxicity results are considered. In addition, the sample PCL 2.5, showed significantly lower Log reduction than S 2.5 (P-value: 0.01). This was due to the absence of PES, which also was mentioned in drug release sections.

Cytotoxicity Test

Optimally, a wound dressing should not release toxic products or produce adverse reactions, which could be evaluated through in vitro cytotoxic tests. One of the most important advantages of bacteria triggered systems is that these systems can reduce possible cytotoxicity by reducing the unneeded release of antibacterial drugs. In the previous section the antibacterial efficacy of the BTAC-loaded nanofibers was analyzed. To gain insight into the impact on cell viability of the nanofibers, human dermal fibroblast cells were exposed to membranes. MTT results for dressings within 24 h contact with fibroblast cells are collected and provided in FIG. 7 and FIG. 8.

Figure 7:
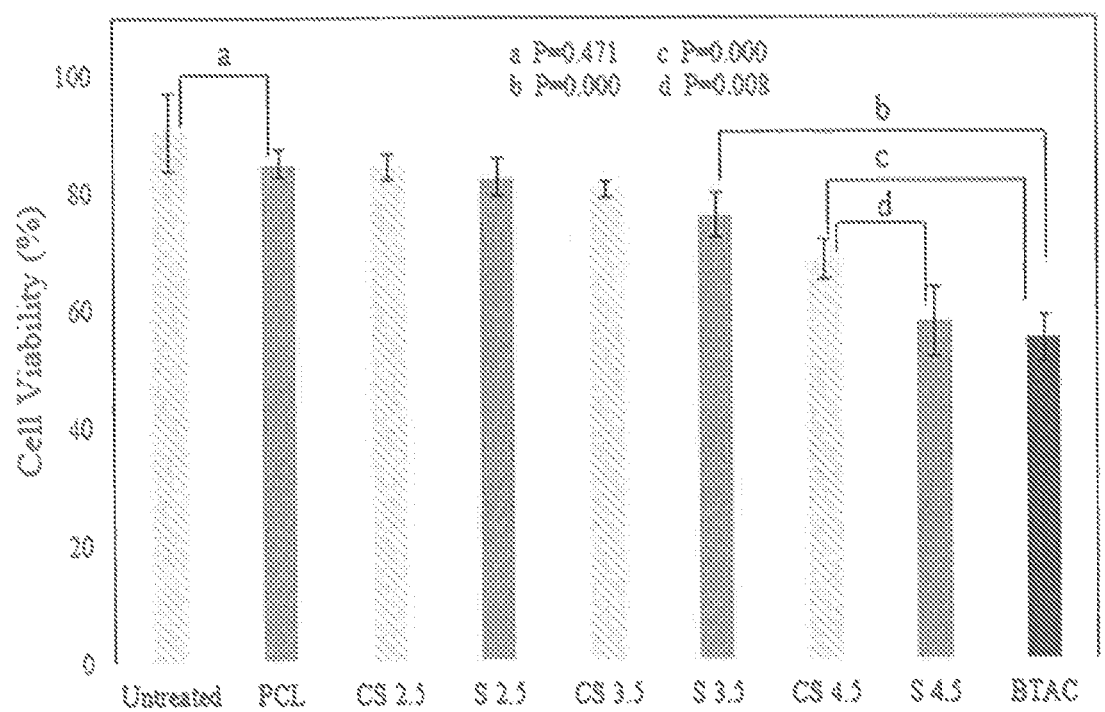
FIG. 7 shows fibroblast cell viability after 24 h of contact with nanofibers.

FIG. 7 shows fibroblast cell viability after 24 h of contact with the nanofibers.

Figure 8:
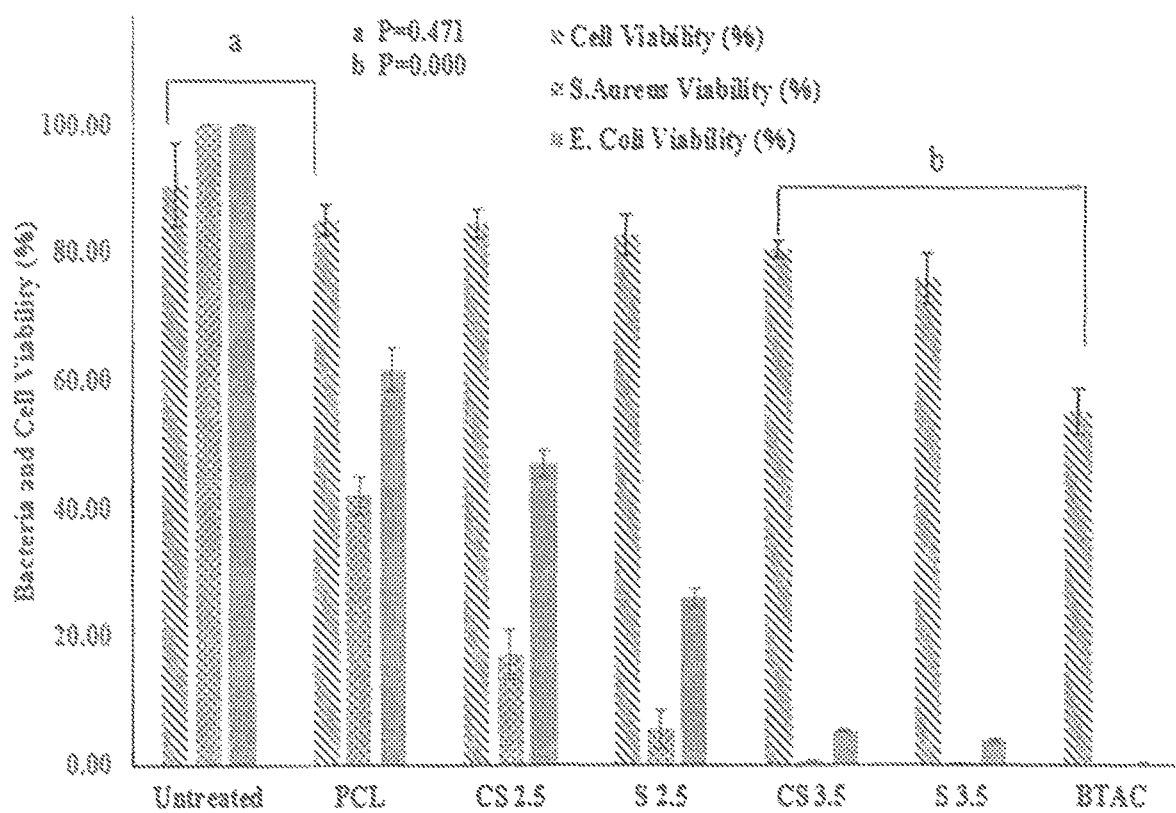
FIG. 8 shows fibroblast, *S. aureus* and *E. coli* viability after 24 h of contact with nanofibers.

FIG. 8 superimposes the data of FIG. 7 for fibroblast cell viability with viability of S. aureus and E. coli over the same period of time, illustrating the lethal effect of the antibacterial nanofibers on microbes without comparable detriment to the fibroblast cells.

Acceptable viability of cells was recorded for most of the samples with and without BTAC. Untreated nanofiber (CS nanofiber with no drug in the core) showed the highest cell viability. There is no significant difference between cell viability of untreated and PCL nanofibers (P=0.471), which indicated the low release of BTAC in PCL nanofibers. The same result was observed in antibacterial test, when there was a significant difference between antibacterial efficacy of PCL and other samples. This result showed higher degradability of PES in response to bacterial activity.

There were no significant differences between cell viability of single and core shell nanofibers with 2.5% and 3.5% BTAC. However, at higher concentration of BTAC a significant difference between cell viability of S 4.5 and CS 4.5 (P=0.008) was observed.

To compare the cell viability of BTAC-loaded nanofibers and free BTAC, an un-encapsulated BTAC was included in the MTT assay. As nanofibers were in contact with fibroblast cells for 24 h, the concentration of BTAC for MTT assay was chosen to be equivalent to the cumulative release of BTAC from S 3.5 within 24 h (34 mg/L). Cell viability of free BTAC showed a significant difference with S 3.5 and even CS 4.5. The lower cell viability of free BTAC was due to the fact that there was no control on the release. According to FIG. 7, BTAC damages almost half of fibroblast cells (55.2±4.0 compared to 80.5±3.8 for CS 3.5). An aim of the technology is to provide the least cytotoxicity in the wound site. Fibroblasts are critical in supporting normal wound healing, involved in key processes such as breaking down the fibrin clot, creating new extra cellular matrix (ECM) and collagen structures to support the other cells associated with effective wound healing, as well as contracting the wound. Besides, although the free drug showed high antibacterial efficacy in the short time assessed, it would not be efficient over a longer time period, since the drug can be easily washed out by wound exudate. With respect to no obvious cytotoxicity shown in the MTT assay, and strong antibacterial activity toward S. aureus and E. coli in vitro, CS 3.5 could be utilized in wound dressing for treatment of chronic wounds.

According to the cell vitality results, it can be concluded that drug in the cell media (even in the 24 h) is not at a cytotoxic level. To have a better understanding, the drug release of S 2.5 was measured in the fibroblast cell supernatant within 1 h. As expected, the percentage of cumulative release in the fibroblast supernatant (11.3±0.5) was significantly lower than in bacteria supernatant (32.2±0.8) (P=0.0001). Thus, it can be concluded that fibroblast cell activity does not initiate the degradation of nanofibers. Further, the pH for fibroblast supernatant was 7 and for the bacteria supernatant, the pH was 5.3. The acidic pH of bacterial supernatant could be the other factor that facilitates the degradation. To test this, the percentage of cumulative release of S 2.5 was measure in a pH=5 buffer within 1 h (12.1±0.4), which was significantly higher than TSB (10.1±0.4), but lower than bacteria supernatant. It can be concluded that both the lipase enzyme activity and an acidic pH play role in the degradation of nanofibers.

S 3.5 and CS 3.5 were repeatedly challenged by fresh 8 Log S. aureus (29213) for 4 times (each for 2 hours). After 2 hours, samples were washed with PBS, immersed in fresh bacterial suspension, and re-suspended. This re-suspension was repeated twice more for a total of 4 challenges.

Table 4 provides the data obtained from the repeated challenge of the nanofiber membranes.

TABLE 4

| | Repeated challenge of the nanofiber membranes | | | | | | | |
|---|---|---|---|---|---|---|---|---|
| | $1^{st}$ 2 h | | $2^{nd}$ 2 h | | $3^{rd}$ 2 h | | $4^{th}$ 2 h | |
| | % | $Log_{10}$ | % | $Log_{10}$ | % | $Log_{10}$ | % | $Log_{10}$ |
| CS 3.5 | 100.0 | 8.8 | 30 ± 14 | 0.2 | 44.9 ± 7.3 | 0.3 | 50.6 ± 2.1 | 0.3 |
| S 3.5 | 100.0 | 8.8 | 60.6 ± 9 | 0.5 | 21.2 ± 9.9 | 0.1 | 24.7 ± 12.3 | 0.1 |

Figure 9:
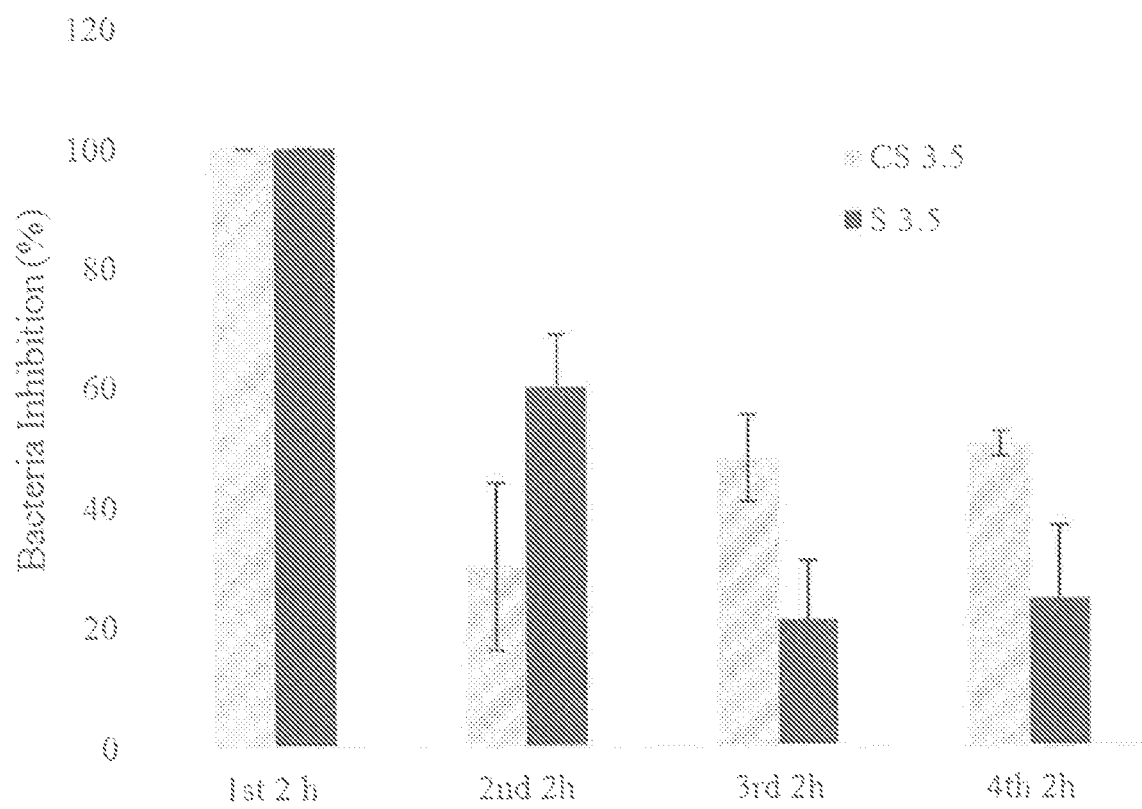
FIG. 9 shows efficacy data after repeated challenge of nanofiber membranes (CS 3.5 and S3.5) with 8 Log *S. aureus* (29213).

FIG. 9 depicts the data of Table 4, showing the repeated challenge of the nanofiber membranes (CS 3.5 and S3.5) with 8 Log *S. aureus* (29213).

Bacteria inhibition of both samples within the first 2 h was 100%. Afterward, the samples were immersed in the new bacteria suspension for the next 2 h, bacteria inhibition of S 3.5 is still higher than CS 3.5 (P=0.033). In the third and fourth repetitions, bacteria inhibition of S 3.5 significantly declined (from 60.6% to 21.2% and 24.7%) and the bacterial reduction by CS 3.5 is significantly higher than S 3.5 (44.9±7.3% versus 21.2±9.9%, p=0.029<0.05; 50.6±2.1% versus 24.7±12.3%, P=0.023<0.05).

The antibacterial efficacy of the core-shell nanofibers was higher than single ones over a prolonged time period, highlighting the advantages of using these fibers in wound healing, and prevention of recurring infections.

Core-shell nanofibers were formed which could be degraded in response to bacteria and provide on-demand antibacterial drug or biocide release. This system showed higher biocide release when in contact with bacteria supernatant than in TSB. More controllable release was shown with core-shell nanofibers than with single ones, which could thus provide a slow, prolonged, efficient bacteria killing activity. Due to selective release of nanofibers, high cell viability was shown in fibroblasts. The efficient antibacterial activity of the nanofibers, without severe cytotoxicity, makes these fibers useful in wound healing applications.

One important application anticipated for the present invention is fabrication of nanofibrous wound dressings that enable wound infection monitoring and on-demand drug delivery. Currently available commercial antimicrobial wound dressings passively deliver biocides to the wound bed even in the absence of pathogens. As recited herein, this has several drawbacks. First, the high level of constant release of biocides can cause extra pain to patients. Second, the majority of biocides have undesirable cytotoxicity to skin cells, leading to delayed wound healing. Also, prolonged subthreshold levels of exposure to biocides can lead to bacterial resistance.

To improve wound care and cut down the occurrence of bacterial resistance, clinicians need to be informed of the presence of bacterial wound infection at the first occurrence, and need the ability to treat and monitor the infection without having to remove the dressing, thereby avoiding the secondary trauma, pain, and extra labor costs associated with dressing changes. Virulence factors secreted by pathogens have been used as triggering factors in a few bacteria-responsive systems. However, the response in these systems is either too low in sensitivity or too slow in identifying bacteria to be of practical value. Commercial dressings combining wound infection monitoring and on-demand drug delivery have not been developed. In one preferred embodiment, the antibacterial core-shell nanofibers provided by the present invention, can be used to fabricate an innovative theranostic antimicrobial dressing that can both report infection with tunable sensitivity and deliver biocides on-demand. This is achieved by fabricating the novel theranostic mats as disclosed herein with a swellable diagnostic shell and a core fiber loaded with biocides. The core-shell structured nanofibers report the presence of bacteria in an unprecedentedly sensitive and prompt manner, and automatically release biocides in response to these bacteria.

High sensitivity and reliability in detecting bacterial infection is achieved by a) electrospinning a novel polymer bearing two reporting dyes into nanofibers to create high surface area in direct contact with the wound; b) adopting a core-shell structure to creatively enrich the color probes on the surface of already very fine nanofibers to maximize the density of those probes on the surface; c) optimizing the density of the fibers for the maximum sensitivity with the least wasted material. Also, to increase the reliability of detection, dyes with colorimetric and fluorescent features are used. The theranostic mats allow patients and frontline staff to monitor the status of the wound with naked eyes, and advanced care providers to evaluate the status with a portable UV lamp for earlier detection. The theranostic mats provide interweaved mechanisms of on-demand release of biocides for automatic treatment of wound infections with different levels of severity. One portion of biocides is bonded to the nanofiber shell via bacterial enzyme cleavable links. Another portion of biocides is incorporated in the core of the core-shell nanofibers. The poly(acrylic acid) (PAA) based shell of the theranostic mats swell in basic pH (due to bacterial infection) to deliver the biocides from the core through diffusion. This novel design can tune the release of biocides through two delivery mechanisms, allowing complex design of drug release profile to suit the needs of varying wounds and patients.

In a preferred embodiment, the present invention provides a unique combination of elements comprising a seamless diagnosis-treatment-feedback system that can be incorporated into a multilayer nanofiber dressing with on-demand, antibacterial components. A multilayer wound dressing will decrease healing time, support tissue repair and regeneration, eliminate painful dressing changes with layered removal, and prevent the onset of bacterial infection with on-demand antibacterial agents. Layered removal leaves the contact layer applied to a wound in place while the outer layers of the dressing are removed. Color changes in the reporting dyes would indicate a response to the presence of bacterial infection. The availability of a practical and convenient wound management system for patients with skin injuries and for example, chronic wounds caused by severe burns, and by pressure, venous, and diabetic ulcers will meaningfully contribute to improving the quality of life for these patients and reducing overall healthcare cost in long term.

In the preceding description, for purposes of explanation, numerous details are set forth in order to provide a thorough understanding of the embodiments. However, it will be apparent to one skilled in the art that these specific details are not required. For example, specific details are not provided as to whether the embodiments described herein are implemented using computer hardware or software, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

The following references are hereby incorporated by reference.

Augustine et al., Electrospun PCL membranes incorporated with biosynthesized silver nanoparticles as antibacterial wound dressings, Appl. Nanosci. 6 (2016) 337-344. doi: 10.1007/s13204-015-0439-1.

Bean et al., Triggered release of Bacteriophage K from agarose/hyaluronan hydrogel matrixes by *Staphylococcus aureus* virulence factors, Chem. Mater. 26 (2014) 7201-7208. doi:10.1021/cm503974 g.

Craig et al., Bacterial protease triggered release of biocides from microspheres with an oily core, Colloids Surfaces B Biointerfaces. 127 (2015) 200-205. doi:10.1016/j.colsurfb.2015.01.036.

He et al., Fabrication of metronidazole loaded poly (c-caprolactone)/zein core/shell nanofiber membranes via coaxial electrospinning for guided tissue regeneration, J. Colloid Interface Sci. 490 (2017) 270-278. doi:10.1016/j.jcis.2016.11.062.

Hoang et al., Degradation of polyethylene succinate (PES) by a new thermophilic Microbispora strain, Biodegradation. 18 (2007) 333-342. doi:10.1007/s10532-006-9067-5.

Thet et al., Prototype Development of the Intelligent Hydrogel Wound Dressing and Its Efficacy in the Detection of Model Pathogenic Wound Biofilms, ACS Appl. Mater. Interfaces. 8 (2016) 14909-14919. doi:10.1021/acsami.5b07372.

Traba & Liang, Bacteria responsive antibacterial surfaces for indwelling device infections, J. Control. Release. 198 (2015) 18-25. doi:10.1016/j.jconrel.2014.11.025.

Xiong et al., Lipase-sensitive polymeric triple-layered nanogel for "on-demand" drug delivery, J. Am. Chem. Soc. 134 (2012a) 4355-4362. doi:10.1021/ja211279u.

Xiong et al., Bacteria-Responsive Multifunctional Nanogel for Targeted Antibiotic Delivery, Advanced Materials, 24(46) December (2012) 6175-6180. doi: 10.1002/adma.201202847.

Yang et al., Promotion of skin regeneration in diabetic rats by electrospun core-sheath fibers loaded with basic fibroblast growth factor, Biomaterials. 32 (2011) 4243-4254. doi:10.1016/j.biomaterials.2011.02.042.

What is claimed is:

1. A core-shell nanofiber comprising:
   a core comprising an antibacterial agent and a biocompatible polymer;
   a shell surrounding the core comprising a bacterially degradable polymer, said bacterially degradable polymer being responsive to bacterial colonization in a wound,
   wherein the shell comprises polycaprolactone (PCL) and poly(ethylene succinate) (PES), said shell further comprising dyes that exhibit a color change when in contact with bacteria.

2. An electrospun nanofiber comprising at least one biocompatible polymer and dyes with colorimetric and fluorescent features that exhibit a color change in response to contact with bacteria.

3. The core-shell nanofiber of claim 1, wherein the bacterially degradable polymer is degradable by bacterial enzyme activity or by a pH of 6 or less.

4. The core-shell nanofiber of claim 3, wherein the enzyme is lipase.

5. The core-shell nanofiber of claim 1, when prepared by the process comprising coaxially electrospinning a fiber to form a core material within a shell material.

6. A nanofiber mat comprising a plurality of core-shell nanofibers according to claim 1.

7. An antibacterial wound dressing comprising the core-shell nanofiber of claim 1.

8. A core-shell nanofiber comprising:
   a core comprising benzyl dimethyl tetradecyl ammonium chloride (BTAC) and poly(vinylpyrrolidone) (PVP); and a diagnostic shell comprising polycaprolactone (PCL) and poly(ethylene succinate) (PES), and dyes with colorimetric and fluorescent features responsive to bacterial contact.

9. The core-shell nanofiber of claim 8, wherein the core comprises BTAC in an amount from 2% to 5% by weight and PVP, and the shell comprises PCL and PES.

10. The nanofiber of claim 2, further comprising an antibacterial agent comprising a quaternary ammonium compound (QAC).

11. A core-shell nanofiber comprising:
    a core comprising a biocompatible polymer;
    a shell surrounding the core comprising a bacterially degradable polymer and dyes with colorimetric and fluorescent features that exhibit a color change in response to bacterial colonization in a wound.

12. The core-shell nanofiber of claim 11, wherein said color change is detectable with naked eyes.

13. The core-shell nanofiber of claim 11, wherein said color change is detectable with a UV lamp.

14. The core-shell nanofiber of claim 11, wherein the core further comprises an antibacterial agent.

* * * * *